US00PP17604P3

(12) United States Plant Patent
Cully et al.

(10) Patent No.: US PP17,604 P3
(45) Date of Patent: Apr. 17, 2007

(54) OAK TREE NAMED 'NADLER'

(50) Latin Name: ***Quercus robur fastigiata*×*Quercus bicolor***
Varietal Denomination: Nadler

(76) Inventors: Earl Cully, 846 Hoagland Rd., Jacksonville, IL (US) 62650; Joshua Daniel Nadler, 20 South Trail, St. Peters, MO (US) 63376

( * ) Notice: Subject to any disclaimer, the term of this patent is extended or adjusted under 35 U.S.C. 154(b) by 0 days.

(21) Appl. No.: 11/050,390

(22) Filed: Feb. 4, 2005

(65) Prior Publication Data

US 2006/0179525 P1 Aug. 10, 2006

(51) Int. Cl.
*A01H 5/00* (2006.01)

(52) U.S. Cl. ..... Plt./225

(58) Field of Classification Search ..... Plt./225
See application file for complete search history.

*Primary Examiner*—Kent Bell
*Assistant Examiner*—June Hwu

(57) ABSTRACT

A new and distinct Hybrid Oak named 'Nadler' characterized by its very narrow habit of growth, its winter hardiness, and hybrid vigor. Also for its beautiful dark green, mildew-resistant foliage and its ability to withstand wind and ice without breakage.

6 Drawing Sheets

The present invention comprises a new and distinct cultivar of a $F_1$ hybrid oak tree, botanically known as *Quercus robur fastigiata*×*Quercus bicolor* (amendment: (*Quercus*× *warei*)) and referred to by the cultivar name 'Nadler'. The parent tree is growing in a cultivated area on the home grounds of inventor Earl Cully, 846 Hoagland Road, eight miles southeast of Jacksonville, Ill., in Morgan County, in Township 14, Range 10. The new cultivar 'Nadler' is the result of seed collected in the fall of 1974 from a tree of *Quercus robur fastigiata* (as determined by Dr. Gary Booth, Department of Horticulture, University of Missouri, Columbia, Mo.). All seedlings grown from seed collected from this one tree proved to be $F_1$ hybrids (amendment: between the female parent *Quercus robur fastigiata* and the male parent *Quercus bicolor*). From an approximate one thousand seedlings, about sixty $F_1$ hybrid seedlings were selected for further evaluation. Out of these sixty hybrid seedlings only two have proven to be worthy of cultivar status. The first to be introduced from this hybrid cross, was the cultivar named 'Long' (U.S. Plant Pat. No. 12,673). 'Nadler' will be the second introduction.

The 'Nadler' cultivar is an extremely narrow-upright form (FIG. 1) that keeps a uniform width nearly to its top. It is very strong wooded with dark green leathery foliage (FIG. 4) that is highly resistant to powdery mildew. It is hardy in Zone 4b and possibly 4a, (U.S.D.A. Hardiness Zone Map). The new 'Nadler' cultivar has been successfully asexually propagated by chip budding onto *Quercus bicolor.* Bud take has been near 95% with no incompatibility between scion and rootstock. Buds set on two year rootstocks have produced six to eight feet of growth in one growing season. Asexually propagated trees of the 'Nadler' cultivar have maintained the unique characteristics which, in combination, distinguish this cultivar selection and from either of its parents, *Quercus robur fastigiata* and *Quercus bicolor* (FIG. 3).

1. The 'Nadler' oak tree at thirty years of age is thirty-five feet in height, with a total limb spread of six feet. The narrow form of the 'Nadler' oak tree will have several uses in the landscape. It can be planted on city streets where a very limited space exists. It could also be planted to form a narrow screen or windbreak. It would lend itself well in a landscape planting where repetition of a columnar architectural form would be desired or it could be planted in a park or on a golf course as a specimen tree.

2. The 'Nadler' oak is highly resistant to wind and ice. It has never suffered any breakage from either wind or ice. Its staminate parent, *Quercus bicolor,* would account for its great strength, as *Quercus bicolor* has the toughest and strongest wood of any of the oaks.

3. Foliage of the 'Nadler' hybrid oak tree is dark green on the upper surface and silvery light green on the undersurface (FIG. 4). This tree has also proven to be highly resistant to powdery mildew.

4. Compared to *Quercus robur fastigiata,* this new hybrid is far more winter hardy. In the thirty years, it has been under evaluation this area has had winter temperatures of minus 28° F. with wind chills to minus 86° F. The 'Nadler' oak tree did not suffer the slightest damage. During October 1991, daytime temperatures were in the fifties and sixties for most of the month. On October 31, the temperature dropped into the teens. On November third, a record low of minus 1° F. was recorded. Many tree species, including the English oak were badly damaged from this Artic blast of air; some were killed to the ground. The 'Nadler' oak tree did not suffer the slightest damage from this blast of frigid air. Based on these winter lows, the 'Nadler' oak tree would be reliably hardy in Zone 4b and possibly 4a (U.S.D.A. Plant Hardiness Map).

5. The 'Nadler' oak exhibits remarkable hybrid vigor. A chip bud set on a two-year old *Quercus bicolor* seedling will make six to eight feet of growth in one growing season.

DETAILED BOTANICAL DESCRIPTION

In the following description, color references are made to The Royal Horticultural Society Colour Chart.

BRIEF DESCRIPTION OF THE DRAWINGS

The accompanying colored photographs illustrate the appearance and color of the new 'Nadler' oak tree. These photographs show the color as accurately as is reasonably possible to obtain in colored reproductions of this type. Actual foliage colors may differ slightly due to light reflectance.

THE PLANT

TREE, HYBRID OAK 'NADLER'

Figure 1:
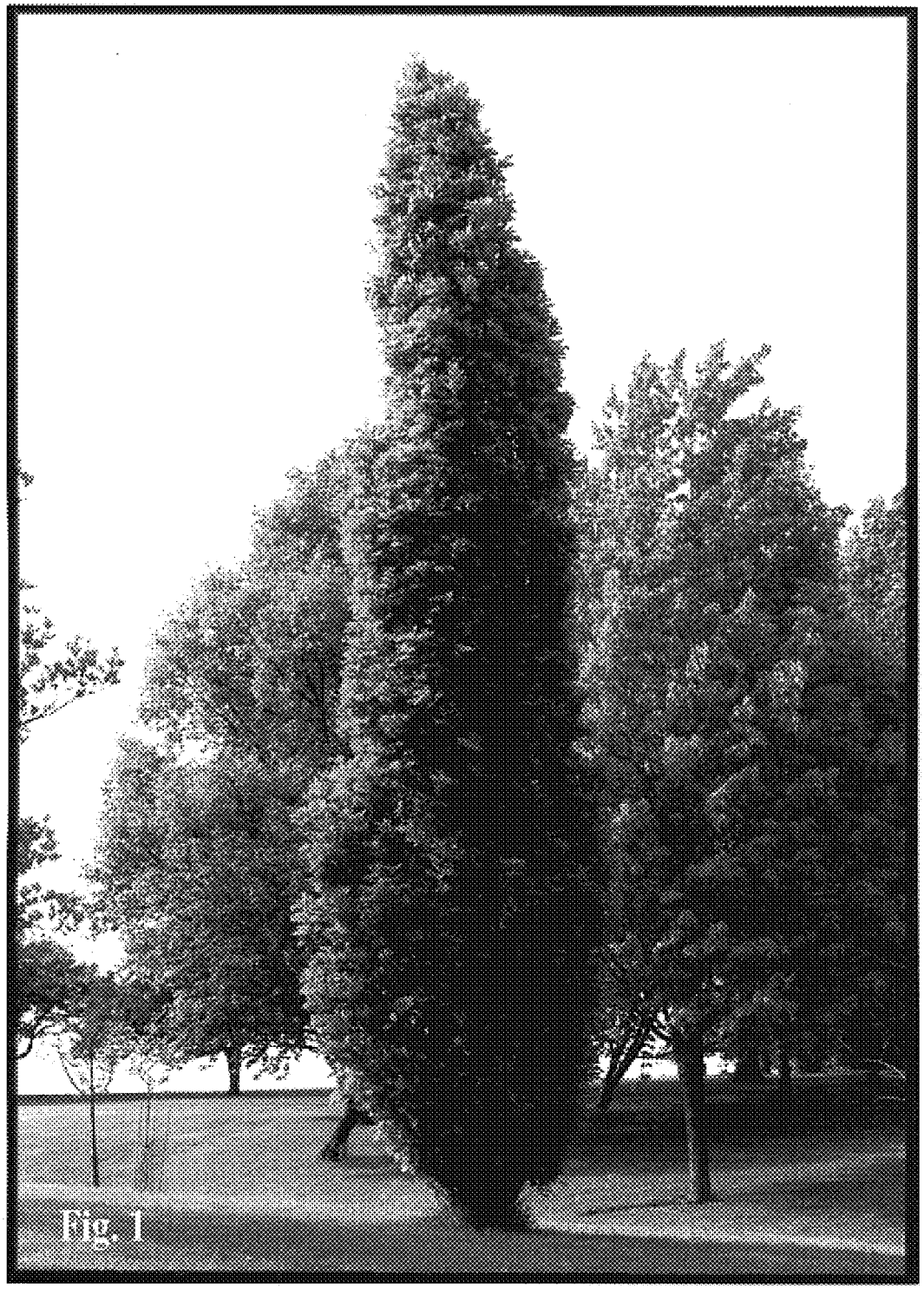
FIG. 1 depicts the initially discovered tree named 'Nadler' in summer foliage showing its very narrow form.
Figure 2:
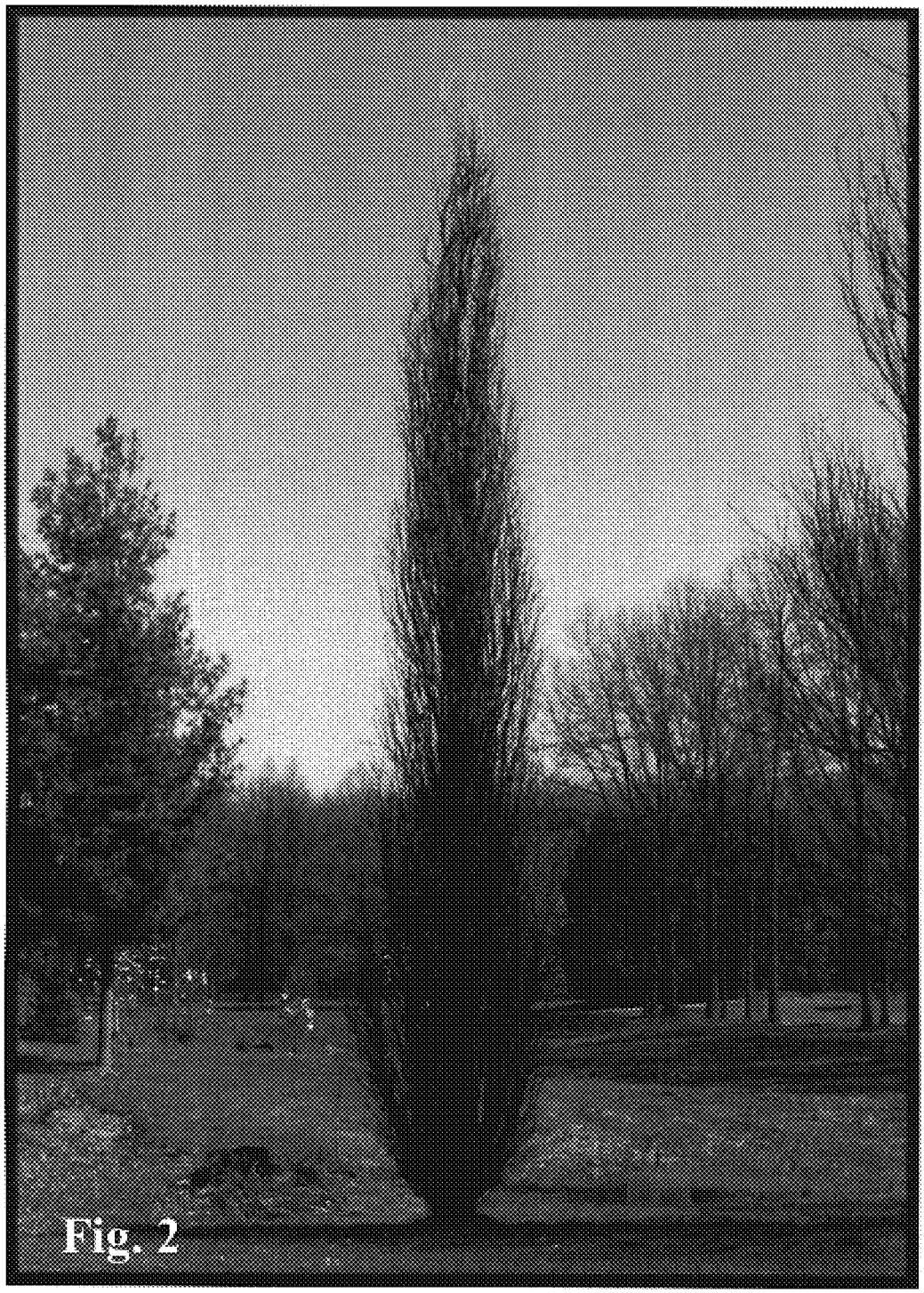
FIG. 2 depicts the 'Nadler' oak tree without foliage.
Figure 3:
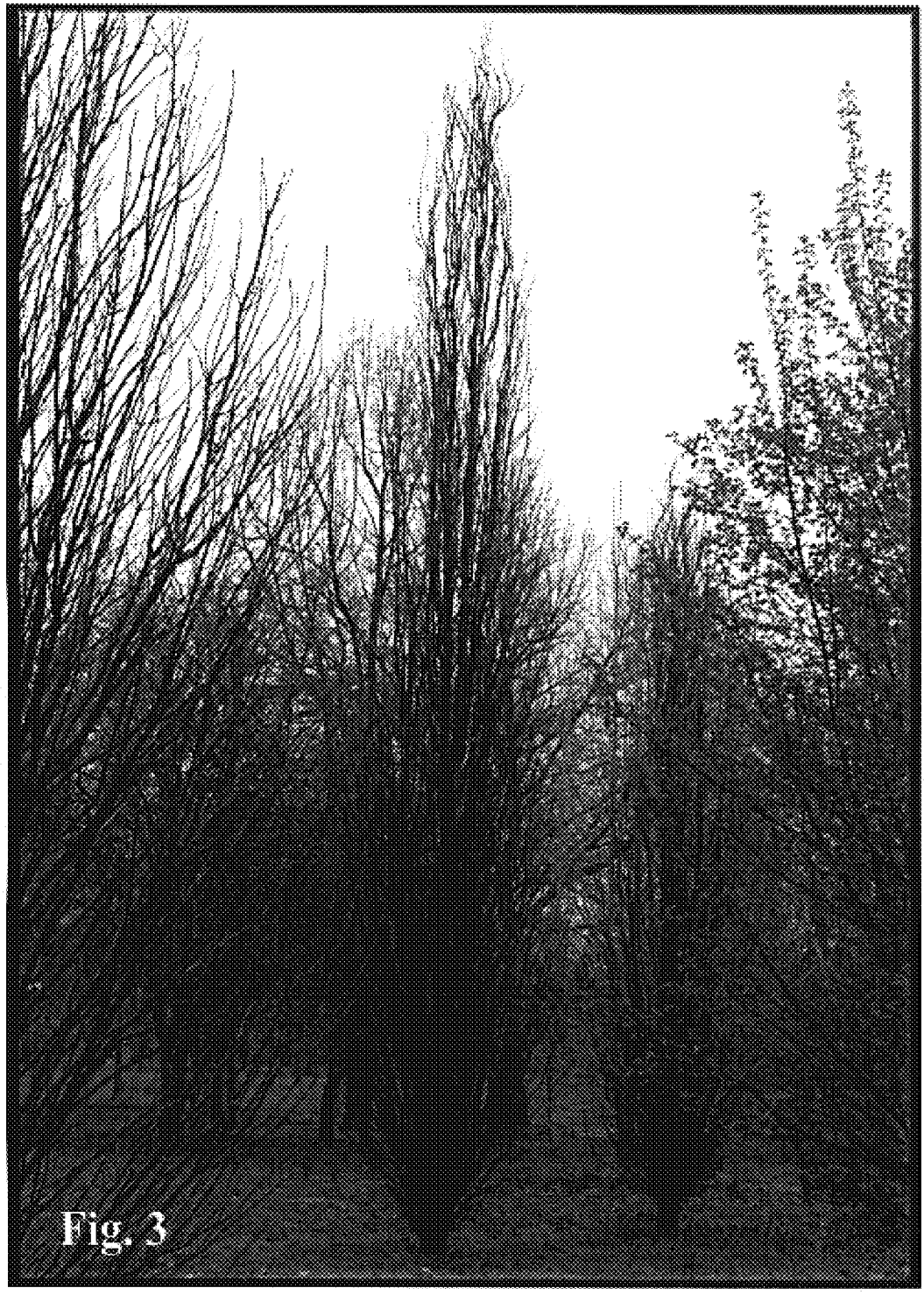
FIG. 3 depicts the first asexually propagated (chip budded) tree of the 'Nadler' cultivar.
Figure 4:
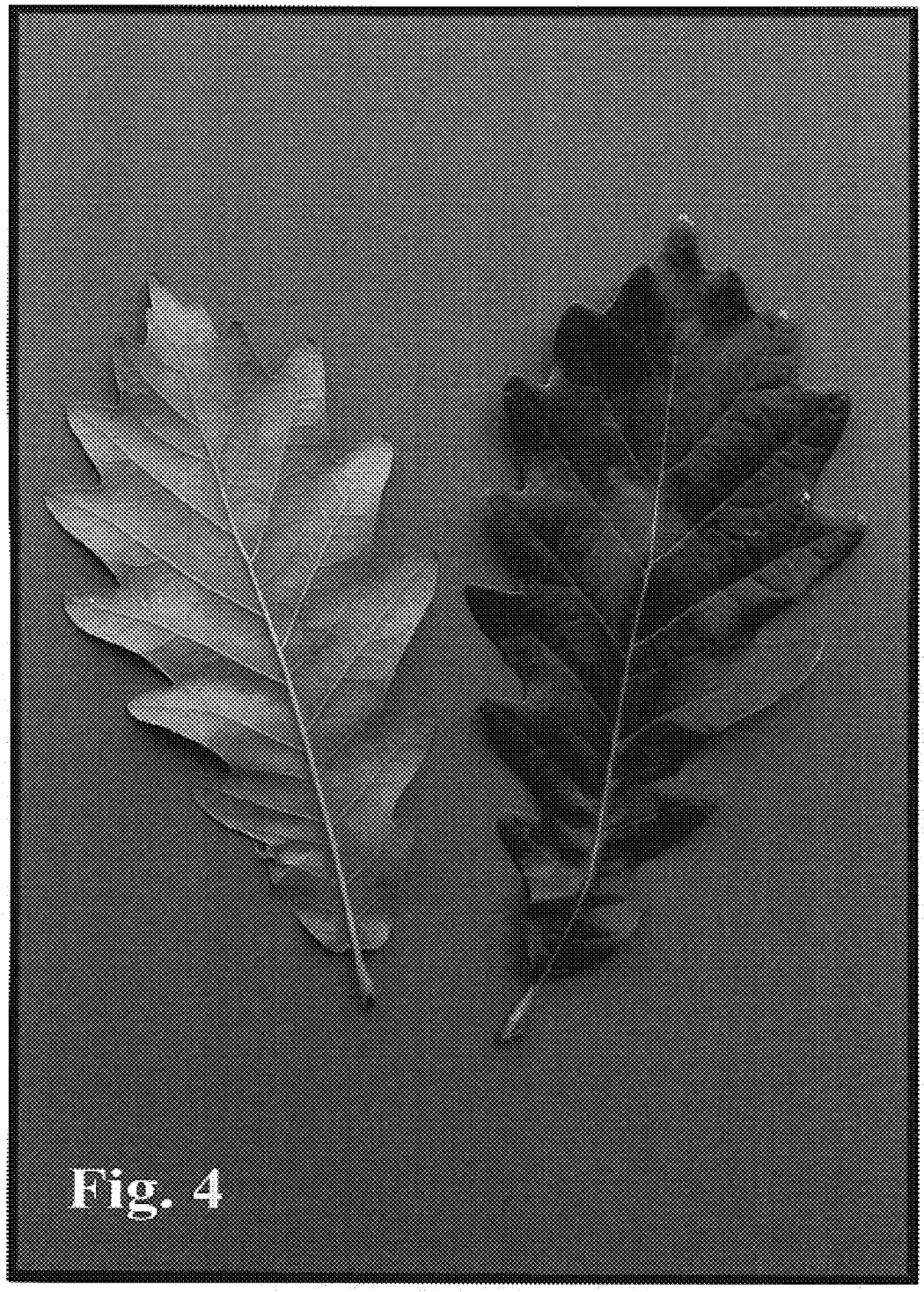
FIG. 4 depicts the foliage of the 'Nadler' cultivar, both upper and lower surface of the leaf and showing the total absence of powdery mildew.
Figure 5:
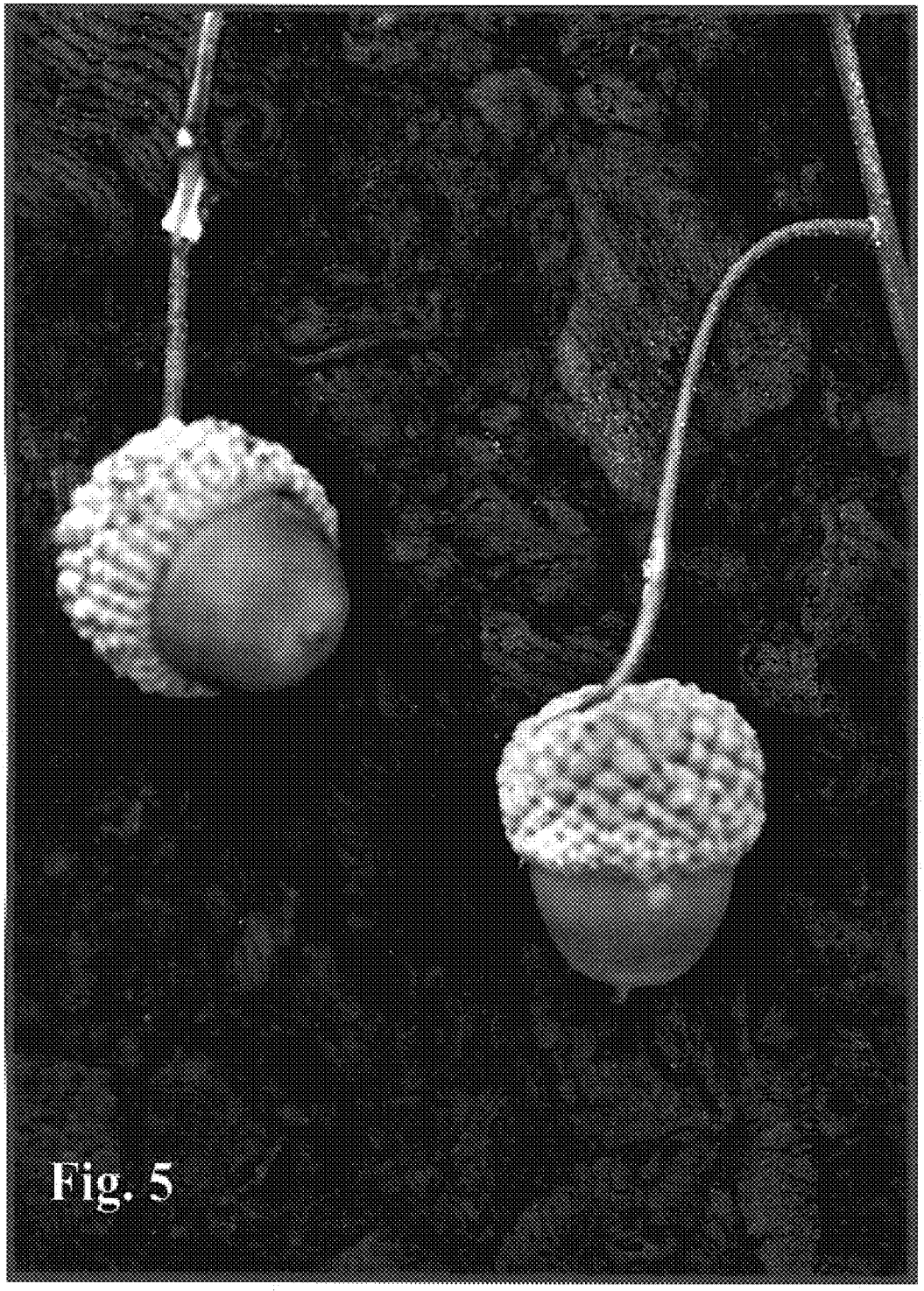
FIG. 5 depicts the mature acorn and peduncle of the 'Nadler' oak in late summer while still green.
Figure 6:
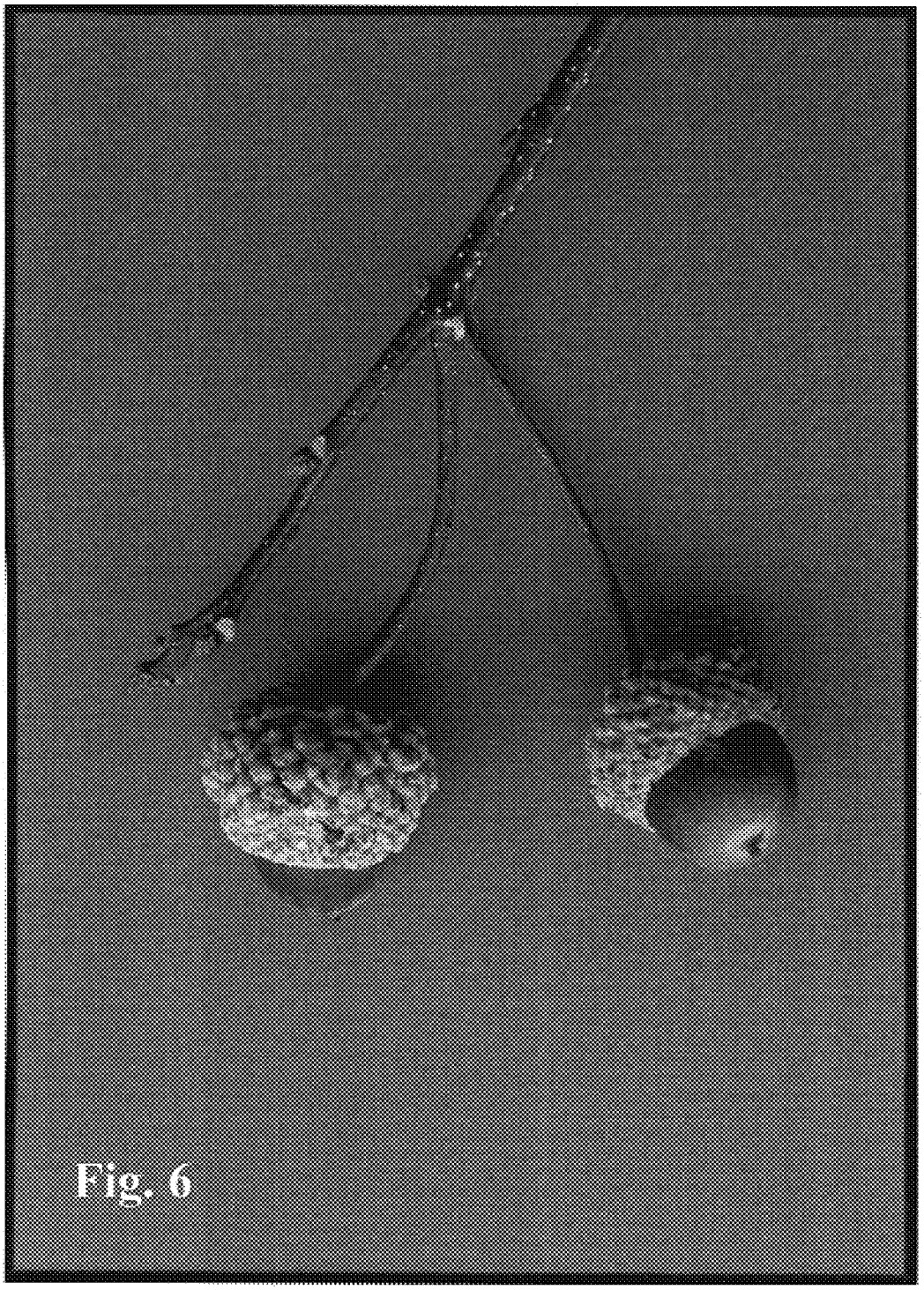
FIG. 6 depicts the stem, including axillary and lateral buds and the mature acorn attached to the peduncle.

Name: Cultivar 'Nadler'.

Parentage: Seedling or Sport: Seedling, (amendment: 1975). Seed parent *Quercus robur* var. *fastigiata*. Pollen parent *Quercus bicolor*.

Classification: *Quercus×warei*. Botanic (name strain) *Quercus robur fastigiata×Quercus bicolor*, Hybrid Oak.

*Where discovered.*—In a cultivated area, at the home of Earl Cully, 846 Hoagland Rd., Jacksonville, Ill., 62650, Morgan County, Township 14, Range 10. This plant has been asexually reproduced by grafting (chip budding) onto Swamp White Oak *Quercus bicolor* seedling rootstock. Presently, propagation is being done in Jacksonville, Ill. and three wholesale nurseries (amendment: in the area of Salem, Oreg. and Portland, Oreg.)

*Form.*—Tree.

*Shape.*—Excurrent, fastigiate.

*Height.*—10.7 m (35'); Spread 1.8 m (6').

*Trunk size(dbh) (amended to.*—(diameter of trunk at 137 cm above ground level)): 27.9 cm (11"); Base: cylindrical.

*Growth rate.*—Moderate.

*Strength.*—Excellent.

*Age.*—30 years from a planted acorn.

*Bark (trunk).*—Bark dark gray to light gray (197 A & B) (amendment: medium-course in texture); small rectangular blocks, size 1.2–2.5 cm (0.5–1.0") (198 A & 197 B & C).

Branches:

*Angle of attachment.*—Most branches between 70° and 80° with a range from 60° to 85°.

*Spacing.*—Dense. Small Twig Bark: (<0.7 cm diameter) (growing season) greenish, smooth (199 A & B) (amendment: (dormant season) gray-brown (197A & B)).

*Lenticels.*—Small (amendment: (μ=0.5 mm)), scattered, round, raised, color (197 B & C).

*Small branch bark.*—(amendment: (0.7–2.5 cm diameter) dark gray (198A), smooth, exfoliation begins at 1 cm in diameter).

Leaves:

*Petiole.*—Length: (0.7–1.2 cm, μ=0.95 cm). Color: green (144B, C, & D). Texture: smooth.

Lamina:

*Length.*—11.5–14.5 cm, (μ=13.3 cm).

*Width.*—5.0–10.4 cm, μ=7.85 cm.

*Form.*—Obovate to obelliptical; base cuneate to slightly auriculate; apex narrowly to broadly acute.

*Margin.*—Coarsely lobed with 6–8 pairs of entire usually obtuse teeth.

*Texture.*—Leathery, glossy, smooth, glabrous above, and (amended to: slightly hairy to woolly beneath.)

*Quantity.*—Abundant.

*Color.*—(Summer) Upper side: dark green (139A & B) amendment: (autumnal) color changes from shades of yellow-green (152A, 153A, & 154A) to brown (199A)).

*Lower side.*—Youngest leaves silver, older leaves are grayish green (191B & C) Ribs and Veins: 6–8 pairs of lobes with 10–12 pairs of veins; (amendment: greenish-yellow (151A, B, & C)).

Buds: (Vegetative). Small (204 mm), blunt, reddish brown, (165A, 166A & B) bud scale margins with irregular tufts of hairs.

Flowers: Typical of oak genus (amendment: Imperfect, plant is monecious; staminate aments are pendent, clustered, length 4.5–8.0 cm (μ=6.0 cm) color of aments, green-yellow (1 C) to yellow-green (154C & D); pistillate flowers found in axils of emerging new leaves, ovary surrounded by a calyx 0.1–0.2 cm in length, purple-red in color (59C & D)).

Fruit: On long peduncle petiole 0.7–1.2 cm, μ=0.95 cm (amended to: 4.0–7.0 cm, μ=5.5 cm;) mostly solitary or with undeveloped second fruit; cap silvery (191B & C) with warty scales (192 between A & C), 0.23–28 cm, μ=0.25 cm wide by 0.15–0.17 cm, μ=0.16 cm deep (amended to: cap is 2.3–2.8 cm, μ=2.5 cm wide by 1.4–1.7 cm, μ=1.5 cm deep); nut brown (199D–200D) 0.23 cm, μ=26 cm long by 0.15–0.19 cm, μ=0.17 cm wide (amended to: 2.3–2.9 cm, μ=2.6 cm long by 1.5–1.9 cm, μ=1.7 cm wide); apex sharp point 2–3 mm; (amendment: shape ovoid; cap encloses nut 30–50%, μ=40%).

Has this plant ever been offered for sale?: No.

Compare this new variety with others of the same species and with its parent or parents; state the distinguishing characteristics of the new cultivar and its advantages. This tree is an extremely narrow-upright form that keeps a uniform width nearly to its top. It is similar to the cultivar 'Skyrocket' English Oak (*Quercus robur* var. *fastigiata*), but is shorter (10.7 m [35'] compared to 13.8 mm [45'] at age 30 and tighter 1.8 m [6'] compared to 4.6 cm [15'] at age 30). (amendment: Swamp white oak (*Quercus bicolor*) the male parent of the 'Nadler' oak tree develops a broad open round-topped crown and a short limby trunk in contrast to the narrow *fastigiate* form of the 'Nadler' cultivar. The 'Long' cultivar is a sister seedling to the 'Nadler' cultivar, but the 'Long' cultivar has a medium-oval crown in comparison to the narrow *fastigiate* form of the 'Nadler' cultivar.) It has bold, dark green, mildew-resistant foliage with highly ornamental silvery lower surfaces similar to its staminate parent. This tree's genetic heritage has made it winter hardy, adaptable to almost any soil, and tolerant of drought and flooding.

It is claimed:

1. A new and distinct cultivar of hybrid oak tree *Quercus robur fastigiata×Quercus bicolor*, named 'Nadler', as illustrated and described.

* * * * *